United States Patent [19]
Attie et al.

[11] Patent Number: 5,521,071
[45] Date of Patent: May 28, 1996

[54] SOLUBLE LDL RECEPTOR AND GENE

[75] Inventors: Alan D. Attie; Stephen L. Sturley; Daniel G. Gretch, all of Madison, Wis.

[73] Assignee: Wisconsin Alumni Research Foundation, Madison, Wis.

[21] Appl. No.: 228,162

[22] Filed: Apr. 15, 1994

Related U.S. Application Data

[63] Continuation of Ser. No. 925,403, Aug. 3, 1992, abandoned.

[51] Int. Cl.$^6$ .......................... C12P 21/02; C12N 15/09; C07K 14/705

[52] U.S. Cl. .................. 435/69.1; 435/235.1; 435/240.1; 435/172.1; 435/240.2; 435/69.6; 530/350; 530/413

[58] Field of Search ........................... 435/252.3, 254.11, 435/240.1, 172.1, 240.2, 235.1, 69.1, 69.6; 530/350, 413; 536/23.1

[56] References Cited

U.S. PATENT DOCUMENTS 4,745,051  5/1988  Smith et al. .............................. 435/68

OTHER PUBLICATIONS

Fischer et al., Science, vol. 262, 250, 1993.
Yamamoto et al., 1984, Cell, 39, 27–38.
Duan et al., 1991, The Journal of Biological Chemistry, 266, 413–418.
Brown and Goldstein, "A Receptor–Mediated Pathway for Cholesterol Homeostasis," 232 *Science* 34–47 (1986).
Esser, et al., "Mutational Analysis of the Ligand Binding Domain of the Low Density Lipoprotein Receptor," 263 *The Journal of Biological Chemistry* 13282–13290 (1988).
Hobbs, et al., "The LDL Receptor Locus in Familial Hypercholesterolemia: Mutational Analysis of a Membrane Protein," 24 *Annual Review of Genetics* 133–170 (1990).
Hobbs, et al., "AvaII polymorphism in the human LDL receptor gene," 15 *Nucleic Acids Research* 379.

Lehrman, et al., "Alu–Alu Recombination Deletes Splice Acceptor Sites and Produces Secreted Low Density Lipoprotein Receptor in a Subject with Familial Hypercholesterolemia," 262 *The Journal of Biological Chemistry* 3354–3361 (1987).
Russell et al., "Different Combinations of Cysteine–rich Repeats Mediate Binding of Low Density Lipoprotein Receptor to Two Different Proteins," 265 *The Journal of Biological Chemistry* 21682–21688 (1989).
Schneider, "The low density lipoprotein receptor," 988 *Biochimica et Biopbysica Acta* 303–317 (1989).
DeLozanne, A., et al., "Effect of Codon Usage in the Expression of Human LDL Receptors" in *Dictyostelium, J. Cell Biol.* 111, No. 5, part 2 p. 87a (1990).
Lehrman, Mark A., et al., "Alu–Alu Recombination Deletes Splice Acceptor Sites and Produces Secreted Low Density Lipoprotein Receptor in a Subject with Familial Hypercholesterolemia," *J. Biol. Chem.* 262:3354–3361 (1987).
Lehrman, Mark A., et al. "The Lebanese Allele at the Low Density Lipoprotein Receptor Locus," *J. Biol. Chem.* 262:401–410 (1987).
Webb, J. C., et al., "Characterization of two new point mutations in the low density lipoprotein receptor genes of an English patient with homozygous familial hypercholesterolemia," *J. Lipid Research* 33:689–698 (1992).

*Primary Examiner*—Stephen G. Walsh
*Assistant Examiner*—Sally P. Teng
*Attorney, Agent, or Firm*—Quarles & Brady

[57] ABSTRACT

A truncation of the human LDL receptor gene has been created which can be expressed in a heterologous host to produce a soluble fragment to the receptor protein. The gene can be expressed in insect cells in culture to produce a protein fragment which is not only water soluble but which also retains affinity for binding to LDL. The truncation is a truncation of the carboxyl terminus of the native LDL receptor gene which results in a 354 amino acid protein fragment designated LDL-R$^{354}$.

13 Claims, 2 Drawing Sheets

SOLUBLE LDL RECEPTOR AND GENE

STATEMENT REGARDING FEDERALLY SPONSORED RESEARCH

This invention was made with United States government support awarded by the National Institute of Health (NIH), Grant No. HL37251. The United States Government has certain rights in this invention.

This application is a continuation of application Ser. No. 07/925,403, filed Aug. 3, 1992, now abandoned.

FIELD OF THE INVENTION

The present invention relates to the general field of molecular biology and relates, in particular, to the isolation and utilization of novel gene fragments to create useful fragments of proteins for therapeutic and research purposes.

BACKGROUND OF THE INVENTION

Cholesterol is an abundant substance in animals because it has an essential function in the membranes of animal cells. Cholesterol is almost completely insoluble in aqueous solution. Within the body other than in membranes, therefore, cholesterol must be carefully segregated from exposure to aqueous environments. Therefore, in multicellular organisms, cholesterol is transported about the body packaged within the hydrophobic cores of plasma lipoproteins. The various plasma lipoproteins in humans have been classified into four major classes, principally by buoyant density. The four major classes are very low density lipoprotein (VLDL), intermediate density lipoprotein (IDL) low density lipoprotein (LDL), and high density lipoprotein (HDL). A fifth class of lipoprotein is chylomicrons, which occur only after feeding. The most abundant cholesterol-carrying lipoproteins in human plasma are of the LDL class, and high levels of LDL circulating in blood plasma are associated with arteriosclerosis and coronary dysfunction. Hence, the mechanisms which purge LDL from the blood stream have been subject to significant study.

In higher animals, LDL is scavenged from the blood stream by receptors located on the cell membranes of animal cells. The receptors are known as the LDL receptor. The structure of the LDL receptor has been generally described, and the gene coding for the production of the receptor has been isolated and sequenced. Descriptions of the LDL receptor, its structure, and its general functionality in interaction with other cellular processes can be found in Schneider, *Bio. Et. Biophys. Acta.*, 988, pages 307–317 (1989) and Hobbs, et al., *Annu. Rev. Genet.*, 24, pages 133–170 (1990). The LDL receptor protein is a cell surface glycoprotein that regulates plasma cholesterol by mediating endocytosis of lipoproteins. The human LDL receptor is a protein of 860 amino acids encoded by a gene which actuates the transcription of an mRNA of 5.3 kb in length. The mRNA of the human LDL receptor gene includes a long 3' untranslated region, as well as a signal peptide which actuates transport of the protein to the plasma membrane, and which is cleaved from the mature form of the protein.

The LDL receptor protein has been characterized as having generally five different domains or regions. One region, referred to as the ligand binding domain, is generally associated with the affinity of the receptor for the two known proteins which are bound by the receptor, ApoB-100, the 550 kd glycoprotein that is the predominant protein of LDL, and ApoE, a 34 kd protein found in multiple copies in IDL and a subclass of HDL. Other domains in the mature LDL receptor protein include an EGF (epidermal growth factor) precursor homology region which, while not specifically necessary for ligand affinity, appears to play a role in the presentation of the LDL receptor to lipoproteins external to the cell. The third domain of the LDL receptor is a region containing clustered O-linked sugar chains. A membrane spanning region of 22 amino acids, of high hydrophobicity, is responsible for the membrane bound nature of the protein. At the carboxyl end of the protein is a domain of 50 amino acids, which extends into the cytoplasm.

While the human LDL receptor gene and the human LDL receptor protein have been studied extensively, this study has been a difficult and, at times, an arduous process. One of the reasons for the difficulty of this study is the inability of researchers to isolate and utilize large quantities of the LDL receptor protein itself. While the protein is produced in significant quantities in animal cells, it is membrane bound and presumably insoluble in aqueous solution. Hence, it is quite difficult to isolate the receptor protein from mammalian tissues in any significant quantity. In addition, since the affinity for membranes is quite strong, it is difficult to express the human LDL receptor protein in heterologous hosts and isolate pure quantities of protein, due to the strong tendency of the protein to associate with membranes in the expression system. In addition, the protein has a complex three dimensional structure, particularly in the ligand binding domain, which is cysteine-rich and includes multiple disulfide bonds. Since the three dimensional structure of the protein is essential for the affinity of the receptor to LDL, production of the protein in hosts which do not properly process proteins subsequent to translation to result in a correct three dimensional structure would not give rise to functional receptor protein.

SUMMARY OF THE INVENTION

The present invention is summarized in that a truncated portion of the human LDL receptor gene has been identified which can be expressed in insect cells in culture to produce a truncated water-soluble form of the LDL receptor protein which binds to, and has specific affinity for, LDL to which the native receptor has affinity.

It is an object of the present invention to describe a gene fragment, and the protein produced from this fragment, which enables the production and accumulation of significant quantities of an LDL receptor fragment which has affinity for and recognizes LDL, and yet which is soluble in aqueous solutions.

It is another object of the present invention to provide a new substance of possible therapeutic value, specifically a soluble LDL receptor protein fragment which can be produced in heterologous hosts for possible clinical, diagnostic, and research use on human systems.

It is a further object of the present invention to elucidate and describe a mechanism by which the active binding portion of the LDL receptor can be created in quantities in heterologous hosts, so as to be useful for further research purposes in further investigating the interaction of the receptor and its target molecules.

It is yet another object of the present invention to describe possible practical applications made possible by the expression of the water-soluble LDL receptor fragment described here.

Other objects, advantages, and features of the present invention will become apparent from the following specification when taken in conjunction with the accompanying drawings.

DETAILED DESCRIPTION OF THE INVENTION

In accordance with the present invention, it has been found that a truncated portion of the gene for human low density lipoprotein receptor (LDL-R) enables the production of a soluble form of the LDL receptor which retains the binding specificity of the native LDL receptor. The expression of this truncated gene in insect cells in culture results in the production of a truncated LDL receptor protein which appears to be conformationally correct, and which, although soluble in aqueous solution, exhibits proper specificity for LDL proteins so as to be useful for LDL binding.

Figure 1:
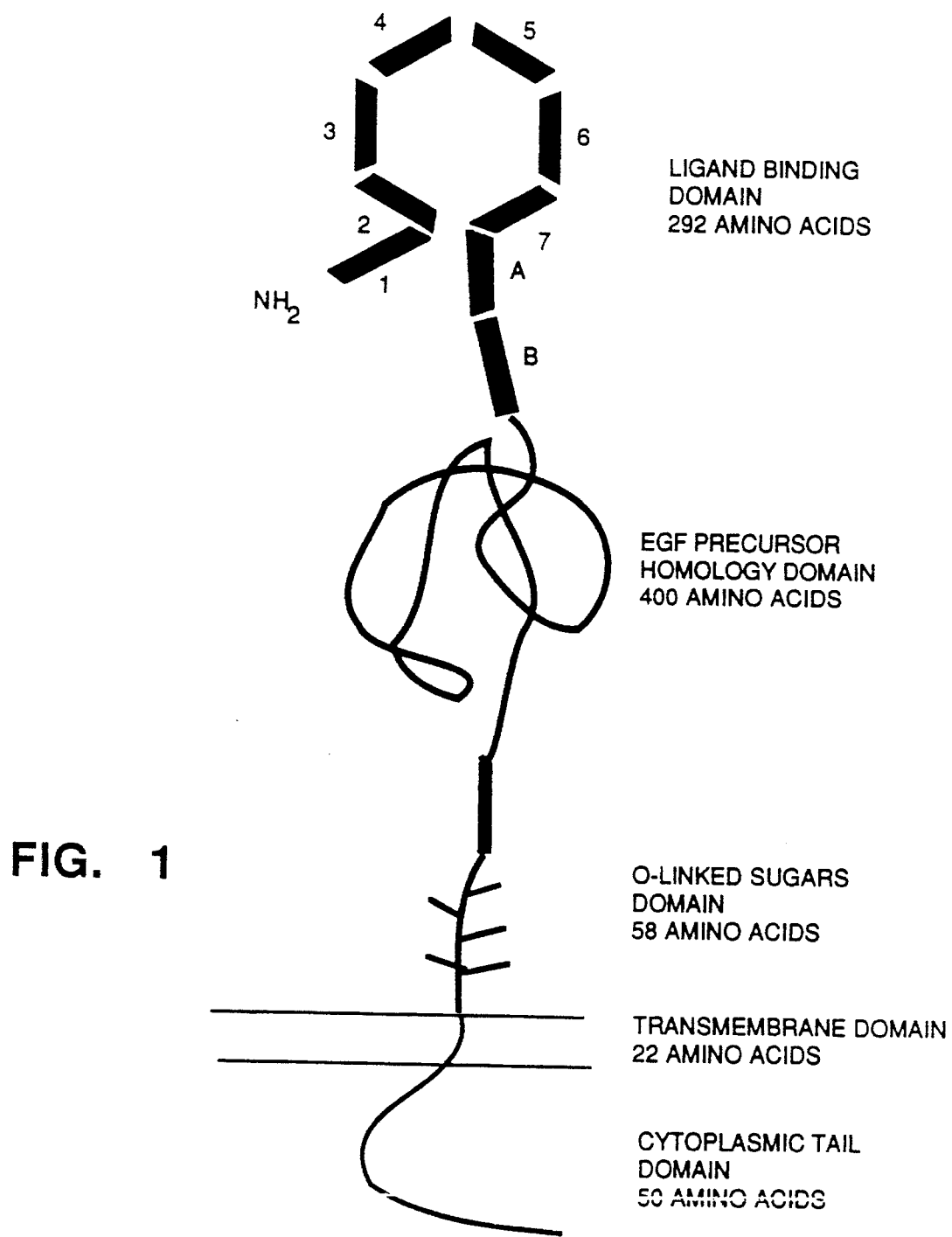
FIG. 1 is a schematic view of the current model for a human LDL receptor protein.
Figure 2:
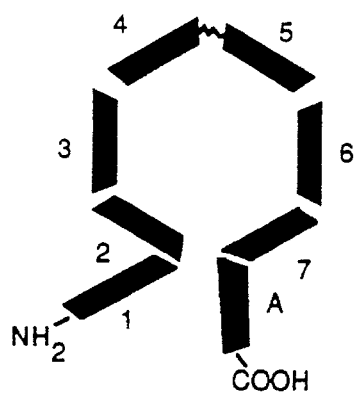
FIG. 2 is a model of the predicted schematic structure of the truncated LDL receptor LDL-R$^{354}$.

The mechanism of the present invention may be best understood by referring first to FIG. 1 which is a graphical illustration of the currently best understood model of the LDL receptor, and the various domains which constitute that protein. The functional domains of the LDL receptor protein had been identified by virtue of homology to other proteins, and also by virtue of the phenotypes of naturally occurring mutants of the protein found in the human population, which have been extensively studied by Brown and Goldstein. Five domains of the mature protein have been characterized. The first is an N-terminal cysteine-rich domain, which is associated with ligand binding, and referred to as the ligand binding domain in FIG. 1. The next region in the protein is a region having homology to the epidermal growth factor (EGF) precursor. The EGF precursor homology domain is required for the acid-dependent disassociation of the lipoproteins from the receptor, during receptor recycling, and also serves to position the ligand-binding domain so that it can bind LDL on the cell surface. The third domain of the protein is a region rich in O-linked carbohydrate. The next region of the protein is a membrane spanning domain, of extremely hydrophobic character, which is the portion of the protein responsible for binding to the animal cell membrane. A cytoplasmic domain at the extreme carboxyl terminus of the protein completes the regions of the protein.

It is previously known that virtually all polymorphisms in the human receptor that are associated with defective binding of LDL reside in the extreme N-terminal cysteine-rich domain. Based on the mutagenic analysis of the LDL receptor as performed by Esser, et al. (*J. Biol. Chem.*, 263:26, pages 13282–13290 (1988)) and Russell, et al. (*J. Biol. Chem.*, 264:36, pages 21682–21688 (1989)), it is clear that all of the seven imperfect repeats which characterize the ligand binding domain are required, or at least involved, in optimal binding to the LDL ligand. Two additional imperfect repeats, designated A and B in FIG. 1, are also found in the EGF precursor homology domain. It seems likely from a similar mutation analysis that repeat A may also facilitate optimal ligand binding.

Based on this understanding, it was decided to attempt a truncation of the full-length LDL receptor gene, to isolate a protein coding sequence encoding for the amino terminal portion of the protein, which would include the expression of all repeats 1 through 7 of the ligand binding domain plus repeat A of the region of EGF precursor homology region. If a host cell expressing this truncated gene were able to facilitate the proper folding of the truncated protein product, then it was possible that the truncated product would retain its ability to bind LDL. Furthermore, the exclusion of the membrane spanning domain could possibly result in secretion of the produced protein. Prior to this attempt, it was not known if a conformationally correct ligand binding domain could be produced without the rest of the native protein. Formation of the correct structure of complex proteins is still poorly understood.

It was previously known that a naturally-occurring mutation of the LDL receptor that deletes the membrane spanning and cytoplasmic domains results in the partial secretion of a truncated receptor, rather than the localization of all of the truncated receptor onto the membrane. However, it is not known if any biological activity of this extracellular mutant receptor has been detected.

By utilization of a restriction endonuclease cleavage site in the commonly available LDL receptor cDNA clone, it was possible to prepare a gene fragment encoding the first 354 amino acids of the mature form of the human LDL-R protein. The polypeptide thus created, designated here LDL-R$^{354}$, could be produced in a foreign host and retain specificity for the LDL molecule. The LDL-R$^{354}$ is also soluble in aqueous solution, and therefore has independent utility in studies of binding to LDL.

As described below, the truncated LDL receptor gene fragment coding for LDL-R$^{354}$ has been introduced, through the use of a recombinant baculovirus, into insect cells grown in culture. It is believed that the utilization of eukaryotic cells in general, and insect cells in particular, is an important factor in the successful production of significant quantities of receptor binding soluble protein. Because the conformational structure of the receptor is critical to its ability to bind to the LDL proteins, if the polypeptide could not be produced in a manner that yielded a properly folded product in heterologous host cells, effective binding would not be possible. It is likely that other eukaryotic host cell systems will result in production of the same protein fragment. However, since the production of proteins of correct conformational character cannot be predicted, particularly for truncated forms of protein, it was not known in advance if a conformationally correct receptor, i.e. one having affinity to the target molecules, could be produced in any host. Nevertheless, the structure of the protein fragment expressed here does seem correct. There is also reason to believe that this particular truncation, with the possible exception of an amino terminal deletion of the very first repeat sequence, is probably the most minimal truncation that would produce active protein. Other truncations which are less severe are likely, based on the evidence presented here, to also express conformationally correct protein fragments. Any such larger truncations could include the EGF precursor homology region without affecting ligand binding, but should not include the hydrophobic membrane spanning domain from the native gene.

The cDNA for human LDL receptor has previously been isolated by others, sequenced, and published. A copy of the 5.3 kb cDNA has been deposited by others with the ATCC and hosted in *E. coli* at Accession Number 57004. From that vector, the region encoding the critical amino terminal 354 amino acid polypeptide can readily be isolated, by a procedure similar to that described below.

Applications of Truncated LDL Receptor

One category of use of the truncated LDL receptor protein is for diagnosis. Presently used diagnostic assays of human serum LDL levels are performed by an indirect estimate method based on a precipitating polyanion used to precipitate LDL with VLDL. The amount of cholesterol in VLDL is estimated by dividing total plasma triglyceride by 5. This method only estimates LDL cholesterol and is incapable of identifying patients who have greater numbers of LDL particles, but only modest hypercholesterolemia, because their LDL particles are simply smaller than the norm, i.e. with less cholesterol per particle. These patients may be even more at risk if, as some data suggest, smaller LDL particles are actually more atherogenic than larger particles. Thus a method of measuring either or both of protein and lipid content of the LDL would be highly desirable. Information as to both lipid and protein would enable estimates to be made of the mean size of LDL particles, which appears to be a clinically useful indication. The truncated LDL receptor described here could be used in binding assays against blood or serum to ascertain actual protein levels and/or numbers of LDL particles.

Another potential advantage of a method of specifically capturing lipoprotein particles containing apoB from the blood would be potential quantitation of Lipoprotein (a), or Lp(a). Lp(a) is a protein covalently attached to the major LDL protein (apoB), and the plasma level of Lp(a) has proven to have a strong correlation with heart disease risk. The plasma level of Lp(a) appears to be both extremely variable and completely determined by genetic factors, and the level of Lp(a) results in a protein product that can vary in size by as much as 20-fold. The immunoassays currently used to quantitate serum Lp(a) are not valid for absolute (i.e. size independent) quantitation. The development of a protocol for binding LDL through the use of the LDL receptor described here, may permit Lp(a) to be measured, since Lp(a) is easily released from apoB by reducing agents which break the linking disulfide bonds.

Another application of the soluble LDL receptor would be for the isolation of plasma LDL for research or clinical purposes. Presently LDL is isolated by preparative ultracentrifugation, which is very costly and requires six days of continuous ultracentrifugation time. A commercially available method or kit for LDL isolation based on this truncated receptor would be popular among LDL researchers, particularly since the receptor recognizes apoB only on LDL and not on VLDL. An advantageous feature of the use of the truncated LDL receptor for affinity selection, rather than an antibody to apoB, is both this selectivity for LDL and also the fact that although the LDL-LDL receptor affinity is quite high, the affinity depends on calcium and can readily be dissipated through the use of a chelating agent such as EDTA. Antibodies to apoB typically require much harsher elution conditions.

Another more dramatic possible application for this receptor would be essentially blood filtering for LDL. The immobilized truncated LDL receptor produced in quantity can be immobilized in a column or cartridge through which a patient's blood could be passed to specifically remove LDL from the blood. The column or cartridge could be regenerated by eluting the LDL. This therapeutic approach seems particularly adapted to kidney dialysis patients, who invariably suffer from hyperlipidemia and who already have their blood dialyzed on a regular basis.

It is also possible to construct alternate LDL-$R^{354}$ expression vectors which condition secretion of the expressed protein fragment. Since the mature protein is initially produced with a signal peptide, which causes transportation of the immature form of the protein to the plasma membrane of the cell which produces the protein, there is every reason to expect that a similar signal peptide strategy can be used to cause secretion of the truncated form of the protein described herein.

EXAMPLES

Construction of Gene.

The construction of the coding sequence for the LDL-$R^{354}$ polypeptide began with a vector designated pRGLDLR-13, which consists of a 1317 base pair XbaI, RsaI fragment from the plasmid pLDLR3 which has been deposited by others with the ATCC as Accession No. 57004. The vector pRGLDLR-13 thus includes a sequence encoding the first 425 amino acids of the LDL receptor, which has been inserted by blunt end ligation into the EcoRV site of pBluescript M13+(Stratagene) 3'-5' orientation. A 14 base pair oligonucleotide (CTAGTCTAGACTAG, New England Biolabs) was used to introduce a translational termination codon in all reading frames, by insertion at the unique EcoRV site in pRGLDLR-13. The EcoRV site corresponds to nucleotide 1076 of the LDL-R cDNA. The resulting plasmid was designated pDL-LDLR. The 5' and 3' termini of the approximately 1317-bp LDL-R fragment from pDL-LDLR was confirmed by DNA sequence analysis. The translation terminating codon was in the predicted reading frame. An 1100 pb BamHI fragment of pDL-LDLR was then ligated to copies of a plasmid pAcYM1, which had been digested with BamHI and treated with alkaline phosphatase. The details of pAcYM1 are described in Matsuura et al. *J. Gen. Virol.* 68:1233–1250 (1987). The resulting construction was designated pAcLDL-$R^{354}$. This transfer vector thus consists of the 5' and 3' sequences from the *Autographa californica* polyhedrin gene which are flanking a protein coding sequence of nucleotides which encodes the first 354 residues of the human LDL receptor, followed by two additional amino acids (leucine and valine), which were introduced at the carboxyl terminus of the peptide by oligonucleotide insertion.

Production of Recombinant Baculovirus.

Copies of the plasmid pAcLDL-$R^{354}$ constructed as described above were co-transfected with the wild-type baculovirus genome (AcNPV) into *Spodoptera fruqiperda* Sf-21 cells. The recombinant viruses (AcNPV-$R^{TM}$) harboring the sequence for the truncated LDL receptor were selected, plaque purified, and titered as described in Summers et al., *A Manual of Methods for Baculovirus Vectors and Insect Cell Culture Procedures*, Tex. Agric. Exp. Stn. Bull. (1987) and Miller et al. in *Genetic Engineering*, Plenum, New York, pp. 277–298 (1986).

Recombinant virus (AcNPV-$R^{354}$) served as the template for a polymerase chain reaction utilizing amplifying oligonucleotides homologous to the 5' and 3' sequences of the *Autographa californica* polyhedrin gene. The resulting amplification product was of a size consistent with the predicted recombination event.

Transfection of Cultured Insect Cells and Recovery of Protein.

The recombinant baculoviruses were then used to infect cells of SF-21 in culture. Quantities of the recombinant baculovirus were infected onto dishes of $4 \times 10^6$ SF-21 cells at a multiplicity of infection of four. Two milliliters of SF-900 (Gibco) medium were harvested from the infected cells 52 hours after infection with the recombinant baculovirus in TCA precipitated media to yield 60 μ gram of protein. Media samples were subjected to sodium dodecyl sulfate, polyacrylamide gel electrophoresis (SDS-PAGE), in the absence or presence of beta-mercaptoethanol, with non-reducing gels of 13.3% acrylamide resolving gel with a 6% stacker and with reducing gels of 10% acrylamide resolving gel with a 4.5% stacker. Immunoblotting was performed using anti-human LDR-R monoclonal antibody C7, and alkaline phosphatase-conjugated goat anti-mouse IgG (Sigma).

Binding Experiments.

Media from transfected SF-21 cells was collected 52 hours after infection and was dialyzed against PBS at pH 7.4. Separately, CHO cells [line TR715-19] previously demonstrated to overexpress the human LDL receptor were grown in Hams nutrient mixture F-12 (Gibco), 20 mM Hepes, pH 7.2, 1% (V/V) fetal calf serum, 4% (V/V) lipoprotein deficient serum (LDS), 2 mM glutamine, and 100 units per milliliter penicillin, 100 μg per ml streptomycin. Twelve hours prior to use, confluent cells were switched to a medium containing Hams F-12, 20 mM Hepes pH 7.2, 5% LDS, 2 mM glutamine, 100 units per ml penicillin, 100 μg per ml streptomycin, 10 μg per ml cholesterol and 0.1 μg per ml 25-hydroxycholesterol. The indicated concentration of dialyzed tissue culture proteins (the concentration was determined by a modified Lowry assay) were incubated with 1.0 μg of [$^{125}$I]-LDL in 2 ml Hams F-12, 20 mM Hepes, pH 7.2 and 5 mg/ml bovine serum albumin, at ambient temperatures for 90 minutes. Samples were equilibrated to 4° C. prior to addition to the CHO cells. The cells were incubated for 3 hours at 4° C. on a rotary shaker, prior to washing, and the release of bound [125I]-LDL by dextran sulfate. Radio iodination of LDL was performed as described previously, e.g. Checovich et al., *Biochem.*, 27:1934 (1988).

Figure 3:
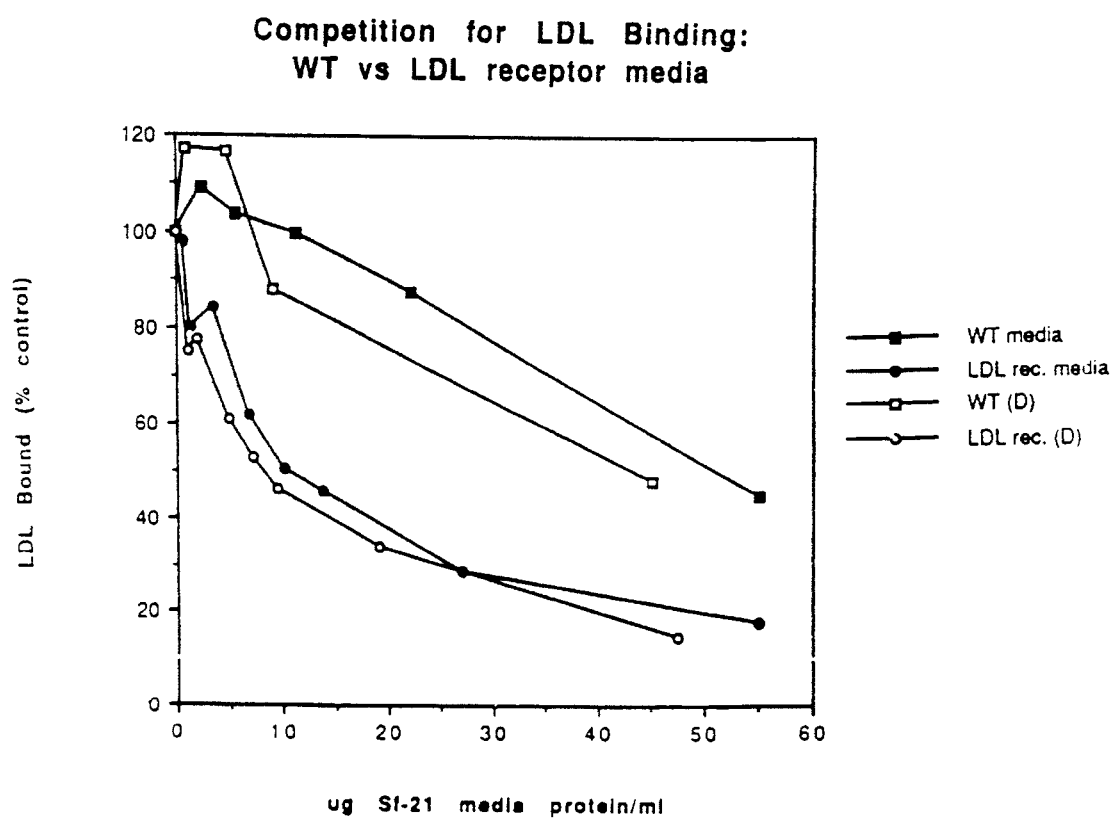
FIG. 3 is a graphical representation of a competition binding assay verifying the binding of the LDL receptor produced in accordance with the present invention with LDL.

The results as illustrated in FIG. 3 indicate that for increasing concentrations of culture media incubated with radiolabeled LDL, in the presence of cells expressing the LDL receptor, the ability of the LDL-R$^{354}$ to specifically bind to LDL was demonstrated. The decrease in cell associated radiolabeled LDL in the presence of increasing concentrations of proteins from the medium of truncated receptor expressing cells demonstrated competitive LDL binding by the protein fragments in the medium. Competitions of similarity severity were not observed with equivalent concentrations of proteins from wild-type virus infected cells.

The results of the immunoblots performed as described above indicate that the peptide fragment which is produced in the infected insect cells described above is secreted, since it is contained with the media extracted from the culture and recognized by the LDL-R specific monoclonal antibody C7. Furthermore, the competitive binding assay indicates that the fragment does correctly bind to the LDL molecule, with a specificity that is at least competitive with the native membrane-bound LDL receptor that is produced in CHO cells. Thus, for the first time, a soluble form of the LDL receptor has been created, and is now made available for use in non-membrane bound research, diagnostic, and therapeutic applications.

We claim:

1. A method of making a water soluble receptor protein fragment having binding affinity for low density lipoprotein in a heterologous eukaryotic host cell comprising the steps of constructing a nucleotide sequence comprising a protein coding sequence coding for a truncated form of a human low density lipoprotein receptor which truncated form includes the first seven amino terminal imperfect sequence repeats and at least one of the two following imperfect sequence repeats of the native human protein but does not include any other portion of the EGF precursor homology domain, and does not include the O-linked sugars domain or the membrane spanning domain of the mature native sequence, and regulatory sequences flanking the protein coding sequence effective to express the protein coding sequence in heterologous eukaryotic host cell;

transforming the nucleotide sequence into the heterologous eukaryotic host cell;

culturing the transformed cell in a medium under conditions favorable to the production of proteins; and isolating the medium containing the receptor protein fragment from the cultured transformed cell.

2. A method as claimed in claim 1 wherein the heterologous eukaryotic host cell is an insect cell in culture.

3. A method as claimed in claim 2 wherein the insect cell in culture is a Sf-21 cell.

4. A method as claimed in claim 2 wherein the nucleotide sequence is introduced into the heterologous eukaryotic host cell through the use of a baculovirus.

5. A method as claimed in claim 1 wherein the protein coding sequence codes for a protein fragment which is truncated after amino acid 354 of the human LDL receptor protein sequence.

6. A method of making a water soluble receptor protein fragment having binding affinity for low density lipoprotein in a heterologous eukaryotic host cell comprising the steps of constructing a nucleotide sequence comprising a protein coding sequence coding for a truncated form of a low density lipoprotein receptor which does not include the membrane spanning domain and the O-linked sugars domain, the truncated form being the protein fragment LDL-R$^{354}$, and regulatory sequences flanking the protein coding sequence effective to express the LDL-R$^{354}$ in a heterologous eukaryotic host cell;

transforming the nucleotide sequence into the heterologous eukaryotic host cell;

culturing the transformed cell in a medium under conditions favorable to the production of proteins; and isolating the medium containing the LDL-R$^{354}$ receptor protein fragment from the cultured transformed cell.

7. A method of using a water soluble protein fragment comprising the steps of (a) constructing a nucleotide sequence comprising a protein coding sequence coding for a truncated form of a human low density lipoprotein receptor gene which truncated form includes the first seven amino terminal imperfect sequence repeats and at least one of the two following imperfect sequence repeats of the native human protein but does not include any other portion of the EGF precursor homology domain, and does not include the O-linked sugars domain or the membrane spanning domain of the mature native sequence, and regulatory sequences flanking the protein coding sequence effective to express the protein coding sequence in a heterologous eukaryotic host cell;

(b) transforming the nucleotide sequence into the heterologous eukaryotic host cell;

(c) culturing the transformed cell in a medium under conditions favorable to the production of proteins;

(d) isolating the medium containing the protein fragment from the cultured transformed cell;

(e) immobilizing the protein fragment on a support; and (f) exposing the immobilized protein fragment on the support to a solution containing low density lipoprotein under conditions which favor the binding of the low density lipoprotein to the immobilized protein fragment until low density lipoprotein binds to the immobilized protein.

8. A method as claimed in claim 7 wherein the heterologous eukaryofic host in step (b) is an insect cell in culture.

9. A method as claimed in claim 8 wherein the insect cells is a sf-21 cell.

10. A method as claimed in claim 7 wherein the nucleotide sequence is transformed into the heterologous eukaryotic host cell in step (b) through the use of a baculovirus.

11. A method as claimed in claim 7 wherein the protein coding sequence encodes a protein fragment which is truncated after amino acid 354 of the human low density lipoprotein protein sequence.

12. A method as claimed in claim 7 wherein the protein fragment is LDL-R$^{354}$.

13. A method as claimed in claim 7 wherein the solution in step (f) is human blood.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 1317 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( v i ) ORIGINAL SOURCE:
        ( A ) ORGANISM: Homo sapiens ( v i i ) IMMEDIATE SOURCE:
        ( B ) CLONE: LDL Receptor ( i x ) FEATURE:
        ( A ) NAME/KEY: CDS
        ( B ) LOCATION: 16..1086

( x i ) SEQUENCE DESCRIPTION: SEQ ID NO:1:

```
CTAGAGGCTG CGAGC ATG GGG CCC TGG GGC TGG AAA TTG CGC TGG ACC GTC        51
               Met Gly Pro Trp Gly Trp Lys Leu Arg Trp Thr Val
                 1               5                   1 0

GCC TTG CTC CTC GCC GCG GCG GGG ACT GCA GTG GGC GAC AGA TGT GAA         99
Ala Leu Leu Leu Ala Ala Ala Gly Thr Ala Val Gly Asp Arg Cys Glu
        1 5                 2 0                 2 5
```

| | | | | | | | | | | | | | | | | |
|---|---|---|---|---|---|---|---|---|---|---|---|---|---|---|---|---|
| AGA | AAC | GAG | TTC | CAG | TGC | CAA | GAC | GGG | AAA | TGC | ATC | TCC | TAC | AAG | TGG | 147 |
| Arg | Asn | Glu | Phe | Gln | Cys | Gln | Asp | Gly | Lys | Cys | Ile | Ser | Tyr | Lys | Trp | |
| | 30 | | | | 35 | | | | | 40 | | | | | | |
| GTC | TGC | GAT | GGC | AGC | GCT | GAG | TGC | CAG | GAT | GGC | TCT | GAT | GAG | TCC | CAG | 195 |
| Val | Cys | Asp | Gly | Ser | Ala | Glu | Cys | Gln | Asp | Gly | Ser | Asp | Glu | Ser | Gln | |
| 45 | | | | | 50 | | | | | 55 | | | | | 60 | |
| GAG | ACG | TGC | TTG | TCT | GTC | ACC | TGC | AAA | TCC | GGG | GAC | TTC | AGC | TGT | GGG | 243 |
| Glu | Thr | Cys | Leu | Ser | Val | Thr | Cys | Lys | Ser | Gly | Asp | Phe | Ser | Cys | Gly | |
| | | | | 65 | | | | | 70 | | | | | 75 | | |
| GGC | CGT | GTC | AAC | CGC | TGC | ATT | CCT | CAG | TTC | TGG | AGG | TGC | GAT | GGC | CAA | 291 |
| Gly | Arg | Val | Asn | Arg | Cys | Ile | Pro | Gln | Phe | Trp | Arg | Cys | Asp | Gly | Gln | |
| | | | 80 | | | | | 85 | | | | | 90 | | | |
| GTG | GAC | TGC | GAC | AAC | GGC | TCA | GAC | GAG | CAA | GGC | TGT | CCC | CCC | AAG | ACG | 339 |
| Val | Asp | Cys | Asp | Asn | Gly | Ser | Asp | Glu | Gln | Gly | Cys | Pro | Pro | Lys | Thr | |
| | | 95 | | | | | 100 | | | | | 105 | | | | |
| TGC | TCC | CAG | GAC | GAG | TTT | CGC | TGC | CAC | GAT | GGG | AAG | TGC | ATC | TCT | CGG | 387 |
| Cys | Ser | Gln | Asp | Glu | Phe | Arg | Cys | His | Asp | Gly | Lys | Cys | Ile | Ser | Arg | |
| | 110 | | | | | 115 | | | | | 120 | | | | | |
| CAG | TTC | GTC | TGT | GAC | TCA | GAC | CGG | GAC | TGC | TTG | GAC | GGC | TCA | GAC | GAG | 435 |
| Gln | Phe | Val | Cys | Asp | Ser | Asp | Arg | Asp | Cys | Leu | Asp | Gly | Ser | Asp | Glu | |
| 125 | | | | | 130 | | | | | 135 | | | | | 140 | |
| GCC | TCC | TGC | CCG | GTG | CTC | ACC | TGT | GGT | CCC | GCC | AGC | TTC | CAG | TGC | AAC | 483 |
| Ala | Ser | Cys | Pro | Val | Leu | Thr | Cys | Gly | Pro | Ala | Ser | Phe | Gln | Cys | Asn | |
| | | | | 145 | | | | | 150 | | | | | 155 | | |
| AGC | TCC | ACC | TGC | ATC | CCC | CAG | CTG | TGG | GCC | TGC | GAC | AAC | GAC | CCC | GAC | 531 |
| Ser | Ser | Thr | Cys | Ile | Pro | Gln | Leu | Trp | Ala | Cys | Asp | Asn | Asp | Pro | Asp | |
| | | | 160 | | | | | 165 | | | | | 170 | | | |
| TGC | GAA | GAT | GGC | TCG | GAT | GAG | TGG | CCG | CAG | CGC | TGT | AGG | GGT | CTT | TAC | 579 |
| Cys | Glu | Asp | Gly | Ser | Asp | Glu | Trp | Pro | Gln | Arg | Cys | Arg | Gly | Leu | Tyr | |
| | | 175 | | | | | 180 | | | | | 185 | | | | |
| GTG | TTC | CAA | GGG | GAC | AGT | AGC | CCC | TGC | TCG | GCC | TTC | GAG | TTC | CAC | TGC | 627 |
| Val | Phe | Gln | Gly | Asp | Ser | Ser | Pro | Cys | Ser | Ala | Phe | Glu | Phe | His | Cys | |
| | 190 | | | | | 195 | | | | | 200 | | | | | |
| CTA | AGT | GGC | GAG | TGC | ATC | CAC | TCC | AGC | TGG | CGC | TGT | GAT | GGT | GGC | CCC | 675 |
| Leu | Ser | Gly | Glu | Cys | Ile | His | Ser | Ser | Trp | Arg | Cys | Asp | Gly | Gly | Pro | |
| 205 | | | | | 210 | | | | | 215 | | | | | 220 | |
| GAC | TGC | AAG | GAC | AAA | TCT | GAC | GAG | GAA | AAC | TGC | GCT | GTG | GCC | ACC | TGT | 723 |
| Asp | Cys | Lys | Asp | Lys | Ser | Asp | Glu | Glu | Asn | Cys | Ala | Val | Ala | Thr | Cys | |
| | | | | 225 | | | | | 230 | | | | | 235 | | |
| CGC | CCT | GAC | GAA | TTC | CAG | TGC | TCT | GAT | GGA | AAC | TGC | ATC | CAT | GGC | AGC | 771 |
| Arg | Pro | Asp | Glu | Phe | Gln | Cys | Ser | Asp | Gly | Asn | Cys | Ile | His | Gly | Ser | |
| | | | 240 | | | | | 245 | | | | | 250 | | | |
| CGG | CAG | TGT | GAC | CGG | GAA | TAT | GAC | TGC | AAG | GAC | ATG | AGC | GAT | GAA | GTT | 819 |
| Arg | Gln | Cys | Asp | Arg | Glu | Tyr | Asp | Cys | Lys | Asp | Met | Ser | Asp | Glu | Val | |
| | | 255 | | | | | 260 | | | | | 265 | | | | |
| GGC | TGC | GTT | AAT | GTG | ACA | CTC | TGC | GAG | GGA | CCC | AAC | AAG | TTC | AAG | TGT | 867 |
| Gly | Cys | Val | Asn | Val | Thr | Leu | Cys | Glu | Gly | Pro | Asn | Lys | Phe | Lys | Cys | |
| | 270 | | | | | 275 | | | | | 280 | | | | | |
| CAC | AGC | GGC | GAA | TGC | ATC | ACC | CTG | GAC | AAA | GTC | TGC | AAC | ATG | GCT | AGA | 915 |
| His | Ser | Gly | Glu | Cys | Ile | Thr | Leu | Asp | Lys | Val | Cys | Asn | Met | Ala | Arg | |
| 285 | | | | | 290 | | | | | 295 | | | | | 300 | |
| GAC | TGC | CGG | GAC | TGG | TCA | GAT | GAA | CCC | ATC | AAA | GAG | TGC | GGG | ACC | AAC | 963 |
| Asp | Cys | Arg | Asp | Trp | Ser | Asp | Glu | Pro | Ile | Lys | Glu | Cys | Gly | Thr | Asn | |
| | | | | 305 | | | | | 310 | | | | | 315 | | |
| GAA | TGC | TTG | GAC | AAC | AAC | GGC | GGT | TGT | TCC | CAC | GTC | TGC | AAT | GAC | CTT | 1011 |
| Glu | Cys | Leu | Asp | Asn | Asn | Gly | Gly | Cys | Ser | His | Val | Cys | Asn | Asp | Leu | |
| | | | 320 | | | | | 325 | | | | | 330 | | | |
| AAG | ATC | GGC | TAC | GAG | TGC | CTG | TGC | CCC | GAC | GGC | TTC | CAG | CTG | GTG | GCC | 1059 |
| Lys | Ile | Gly | Tyr | Glu | Cys | Leu | Cys | Pro | Asp | Gly | Phe | Gln | Leu | Val | Ala | |
| | | 335 | | | | | 340 | | | | | 345 | | | | |

```
CAG CGA AGA TGC GAA GAT CTA GTC TAGACTAGAT CGATGAGTGT CAGGATCCCG    1113
Gln Arg Arg Cys Glu Asp Leu Val
        350                 355

ACACCTGCAG CCAGCTCTGC GTGAACCTGG AGGGTGCTAC AAGTGCCAGT GTGAGGAAGG   1173

CTTCCAGCTG ACCCCACAC  GAAGGCCTGC AAGGCTGTGG TCCATCGCCT ACCTCTTCTT   1233

CACCAACCGG CACGAGGTCA GGAAGATGAC GCTGGACCGG AGCGAGTACG AATTCCTGCA   1293

GCCGGGGGTC CGCTAGTTCT AGAA                                          1317
```

(2) INFORMATION FOR SEQ ID NO:2:

(i) SEQUENCE CHARACTERISTICS:
       (A) LENGTH: 356 amino acids
       (B) TYPE: amino acid
       (D) TOPOLOGY: linear (ii) MOLECULE TYPE: protein (xi) SEQUENCE DESCRIPTION: SEQ ID NO:2:

```
Met Gly Pro Trp Gly Trp Lys Leu Arg Trp Thr Val Ala Leu Leu Leu
 1               5                  10                  15

Ala Ala Ala Gly Thr Ala Val Gly Asp Arg Cys Glu Arg Asn Glu Phe
            20                  25                  30

Gln Cys Gln Asp Gly Lys Cys Ile Ser Tyr Lys Trp Val Cys Asp Gly
        35                  40                  45

Ser Ala Glu Cys Gln Asp Gly Ser Asp Glu Ser Gln Glu Thr Cys Leu
    50                  55                  60

Ser Val Thr Cys Lys Ser Gly Asp Phe Ser Cys Gly Gly Arg Val Asn
65                  70                  75                  80

Arg Cys Ile Pro Gln Phe Trp Arg Cys Asp Gly Gln Val Asp Cys Asp
                85                  90                  95

Asn Gly Ser Asp Glu Gln Gly Cys Pro Pro Lys Thr Cys Ser Gln Asp
            100                 105                 110

Glu Phe Arg Cys His Asp Gly Lys Cys Ile Ser Arg Gln Phe Val Cys
        115                 120                 125

Asp Ser Asp Arg Asp Cys Leu Asp Gly Ser Asp Glu Ala Ser Cys Pro
    130                 135                 140

Val Leu Thr Cys Gly Pro Ala Ser Phe Gln Cys Asn Ser Ser Thr Cys
145                 150                 155                 160

Ile Pro Gln Leu Trp Ala Cys Asp Asn Asp Pro Asp Cys Glu Asp Gly
                165                 170                 175

Ser Asp Glu Trp Pro Gln Arg Cys Arg Gly Leu Tyr Val Phe Gln Gly
            180                 185                 190

Asp Ser Ser Pro Cys Ser Ala Phe Glu Phe His Cys Leu Ser Gly Glu
    195                 200                 205

Cys Ile His Ser Ser Trp Arg Cys Asp Gly Gly Pro Asp Cys Lys Asp
    210                 215                 220

Lys Ser Asp Glu Glu Asn Cys Ala Val Ala Thr Cys Arg Pro Asp Glu
225                 230                 235                 240

Phe Gln Cys Ser Asp Gly Asn Cys Ile His Gly Ser Arg Gln Cys Asp
                245                 250                 255

Arg Glu Tyr Asp Cys Lys Asp Met Ser Asp Glu Val Gly Cys Val Asn
            260                 265                 270

Val Thr Leu Cys Glu Gly Pro Asn Lys Phe Lys Cys His Ser Gly Glu
    275                 280                 285

Cys Ile Thr Leu Asp Lys Val Cys Asn Met Ala Arg Asp Cys Arg Asp
    290                 295                 300
```

```
Trp  Ser  Asp  Glu  Pro  Ile  Lys  Glu  Cys  Gly  Thr  Asn  Glu  Cys  Leu  Asp
305                      310                      315                      320

Asn  Asn  Gly  Gly  Cys  Ser  His  Val  Cys  Asn  Asp  Leu  Lys  Ile  Gly  Tyr
               325                      330                      335

Glu  Cys  Leu  Cys  Pro  Asp  Gly  Phe  Gln  Leu  Val  Ala  Gln  Arg  Arg  Cys
               340                      345                      350

Glu  Asp  Leu  Val
               355
```